US00RE41744E

(19) United States
(12) Reissued Patent
Doyle

(10) Patent Number: US RE41,744 E
(45) Date of Reissued Patent: Sep. 21, 2010

(54) RAMAN PROBE HAVING A SMALL DIAMETER IMMERSION TIP

(75) Inventor: Walter M. Doyle, Laguna Niguel, CA (US)

(73) Assignee: Axiom Analytical, Inc., Tustin, CA (US)

(21) Appl. No.: 11/732,827

(22) Filed: Apr. 4, 2007

Related U.S. Patent Documents

Reissue of:
(64) Patent No.: 6,876,801
Issued: Apr. 5, 2005
Appl. No.: 10/459,004
Filed: Jun. 10, 2003

U.S. Applications:
(60) Provisional application No. 60/387,521, filed on Jun. 10, 2002.

(51) Int. Cl.
*G02B 6/06* (2006.01)
*G01J 3/44* (2006.01)

(52) U.S. Cl. ..... 385/117; 385/39; 385/115; 600/473; 356/301

(58) Field of Classification Search ..... 385/12, 385/39, 115–120; 600/407, 473, 476, 478, 600/326; 356/301, 328
See application file for complete search history.

(56) References Cited

U.S. PATENT DOCUMENTS

| | | | | | |
|---|---|---|---|---|---|
| 5,112,127 | A | * | 5/1992 | Carrabba et al. | 356/301 |
| 5,615,673 | A | | 4/1997 | Berger et al. | |
| 5,652,810 | A | | 7/1997 | Tipton et al. | |
| 5,864,397 | A | * | 1/1999 | Vo-Dinh | 356/301 |
| 5,953,120 | A | * | 9/1999 | Hencken et al. | 356/339 |
| 5,983,125 | A | | 11/1999 | Alfano et al. | |
| 6,310,686 | B1 | | 10/2001 | Jiang | |

* cited by examiner

*Primary Examiner*—Hemang Sanghavi
(74) *Attorney, Agent, or Firm*—Myers Andras Sherman LLP; Joseph C. Andras

(57) ABSTRACT

A probe for use in Raman spectroscopy that can be inserted into a chemical vessel through a small diameter fitting while maximizing the amount of Raman shifted radiation collected and minimizing spurious effects.

22 Claims, 8 Drawing Sheets

RAMAN PROBE HAVING A SMALL DIAMETER IMMERSION TIP

Matter enclosed in heavy brackets [ ] appears in the original patent but forms no part of this reissue specification; matter printed in italics indicates the additions made by reissue.

This patent application claims the benefit of provisional patent application No. 60/387,521, filed on Jun. 10, 2002.

BACKGROUND OF THE INVENTION

1. Field of the Invention

This invention relates generally to spectroscopy and, more particularly, to a Raman probe having a small diameter immersion tip.

2. Description of the Related Art

Molecular spectroscopy is a family on analytical techniques that provide information about molecular structure by studying the interaction of electromagnetic radiation with the materials of interest. In most of these techniques, the information is generally obtained by studying the absorption of radiation as a function of optical frequency. Raman spectroscopy is unique in that it analyzes the radiation that is emitted (or scattered) when the sample is irradiated by an intense optical signal consisting of a single frequency, or a narrow range of frequencies. In this case the "Raman scattering" signal is essentially an emission spectrum with frequency dependent intensities. The individual bands in this spectrum are shifted from the frequency of the excitation signal by amounts that are related to the structure of the molecules present in the sample.

Many different probe designs have been proposed for use in Raman spectroscopy. Some examples are given in I. R. Lewis & P. R. Griffiths, "Raman Spectroscopy with Fiber-Optic Sampling", Applied Spectroscopy. Vol. 50, pg. 12A, 1996, FIGS. 3 through 11. These fall into two general categories. The first category includes probes that use separate optical fibers to transmit radiation to and from the sample. Such "internal fiber probes" can be made quite small in diameter. However, they are deficient in that their design generally does not allow the use of optical filtering between the sample and the fibers to filter out the spurious Raman signals produced in the fiber. The second category includes probes which do not use internal fibers but which employ optical means to superimpose the path of the laser excitation beam and the receiving path for transmission two and from the sample. Although these probes are often employ optical fibers for coupling to the laser source and the spectrometer, their design allows for the use of filtering between these fibers and the sample. They are often referred to as "externally filtered" or "fully filtered" probes. A specific purpose of my invention is thus the design and construction of a fully filtered probe which is suitable for insertion into small volume chemical reaction vessels. I have been told verbally that previous attempts to design small diameter, fully filtered probes have been unsuccessful. This may be due to the fact that most previous probe designs have superimposed the transmitted and received paths in such a way that they are both collimated and have approximately the same diameters at the point where they are combined. This turns out to be a poor choice of conditions for a small diameter probe.

Model RFP-480 Raman Probe introduced in the year 2000 by my company, Axiom Analytical, employs a unique design in which a collimated laser beam is injected into the center of the receiving beam area by means of a rhomboid prism (see FIG. 1). This approach provides ease of optical alignment by taking advantage of the fact that the rhomboid can be fabricated with its two reflecting surfaces highly parallel. However, in order to avoid blocking a significant portion of the received signal, the areas of both the rhomboid and the injected laser beam are made quite small. As will be seen below, the use of a small diameter laser excitation beam provides the first step toward the successful design of a probe with an extended-length small diameter immersion tip. However, in the standard RFP-480, both the transmitted and received beams are nominally collimated in the beam-combining plane and inner diameter of the lightguide in the immersion tip is necessarily set approximately equal to the diameter of the lens which focuses the Raman shifted radiation onto the receiving optical fiber. I will show below that different considerations apply when it is necessary for the probe to have a small diameter immersion tip that can be inserted a substantial distance into a chemical mixture.

SUMMARY OF THE INVENTION

The purpose of this invention is to provide a probe for use in Raman spectroscopy that can be inserted into a chemical vessel through a small diameter fitting while maximizing the amount of Raman shifted radiation collected and minimizing spurious effects.

The invention resides in an immersion probe for use in Raman spectroscopy which includes an extended immersion tip that includes an internally reflecting lightguide, first optical element for collecting laser radiation emerging from a first optical fiber and directing it, after subsequent reflections, into the end of said internally reflecting lightguide in such a way that it is as nearly collimated as possible consistent with substantially all of the radiation entering the lightguide, second optical element for collecting Raman shifted radiation emerging from said internally reflecting light guide and focusing it on a second optical fiber in such a way that the size and shape of the image of the end of the lightguide matches the size and shape of said second optical fiber, and reflecting means for redirecting the beam formed by said first optical element so that its axis is anti-parallel to and coaxial with the axis of the Raman shifted radiation emerging from said lightguide. In an alternative embodiment, the received beam is redirected rather than the transmitted beam.

DETAILED DESCRIPTION OF THE PREFERRED EMBODIMENTS

Figure 1:
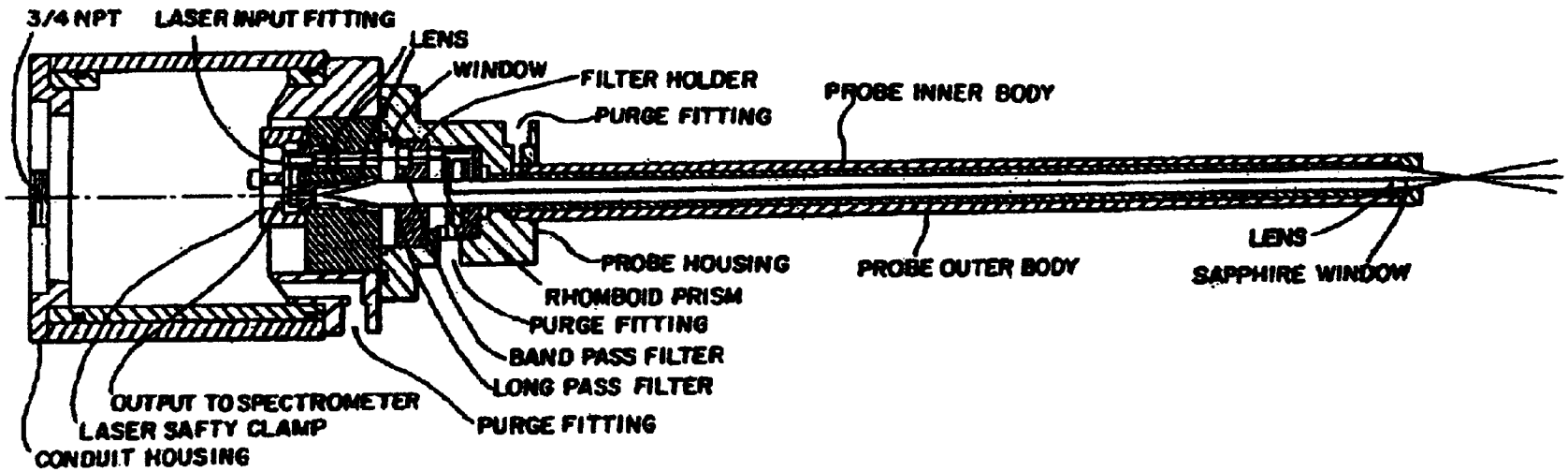
FIG. 1 PRIOR ART
FIG. 1 is a cross-sectional view of a prior art Raman Probe in which a collimated laser beam is injected into the center of the receiving beam area by means of a rhomboid prism.
Figure 2:
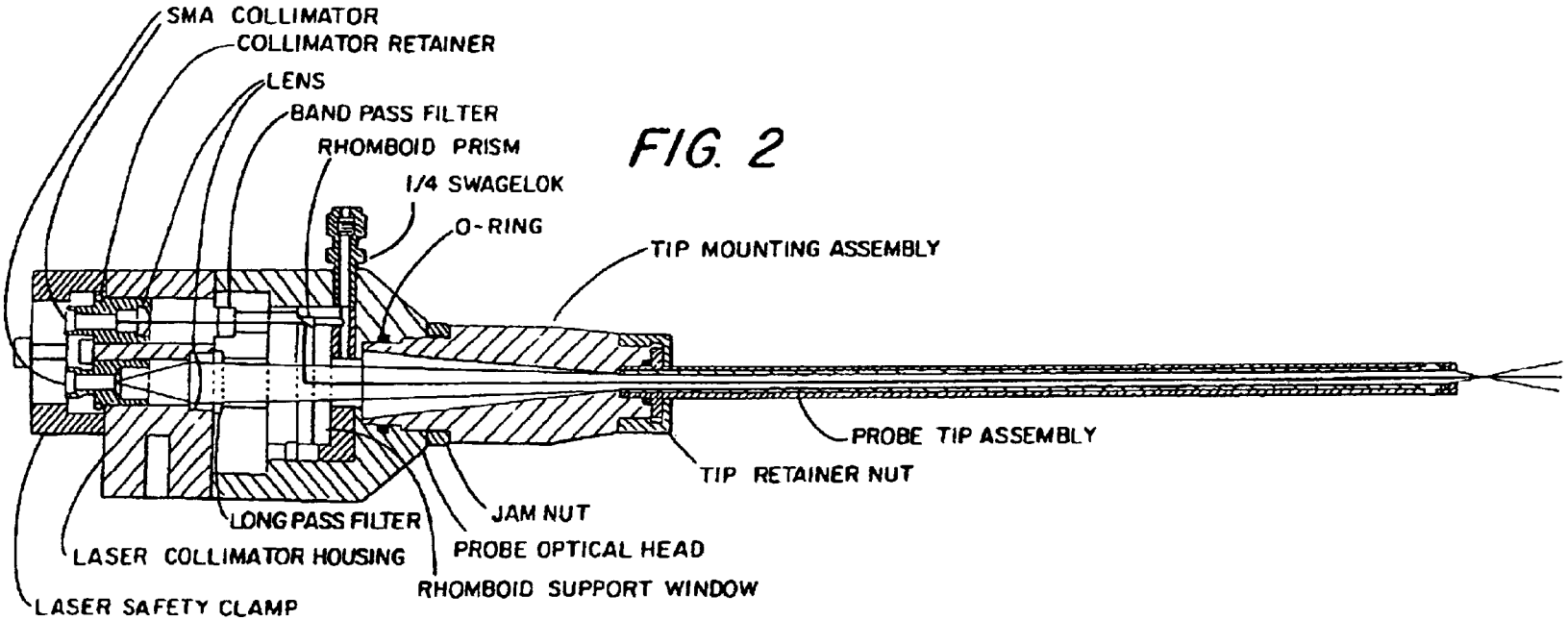
FIG. 2 is a cross-sectional view of an immersion probe of Raman-Spectroscopy immersion probe in accordance with a preferred embodiment of the invention.

A specific embodiment of my invention is shown in FIG. 2, an assembly drawing of the Axiom Analytical RFP-420 immersion probe, introduced during 2001. In this design, the laser radiation emerging from the excitation optical fiber is formed into an approximately collimated beam by a lens that has a short enough focal length so that the collimated beam is no more than about 3 mm in diameter. A small rhomboid doubly reflecting prism is then used to displace this beam to the axis of the probe and to direct it along this axis to the small diameter lightguide which is contained within the probe immersion tip. The received Raman-shifted radiation that has been collected by the objective lens at the end of the immersion tip has a substantially greater range of divergence angles than the nearly collimated laser beam as it travels through the lightguide. A typical ray is thus reflected one or more times by the lightguide wall. Such a ray will emerge from the lightguide at a sufficient angle from the axis so that it misses the angled reflecting surface of the rhomboid a passes on toward the receiving optical fiber. A collection lens, which is significantly larger in diameter than laser beam, is then used to focus this radiation on the receiving fiber. A key element of the invention is the fact that the collection lens images the end of the lightguide on the optical fiber. In contrast, the laser beam collimating lens is configured to produce a small diameter beam which is nearly collimated as is consistent with all of the radiation entering the lightguide. The various elements of this design will be discussed below.

In developing my invention, my specific objective was first to optimize the transfer of radiation from the laser excitation fiber to the sample contained in a small vessel and second to optimize both the collection of Raman shifted radiation from the sample and the transfer of this radiation to the receiving fiber. To see how this is done, we need to consider the interaction of the various requirements. First, we will consider the transfer of radiation to the sample through a small diameter lightguide.

Figure 3:
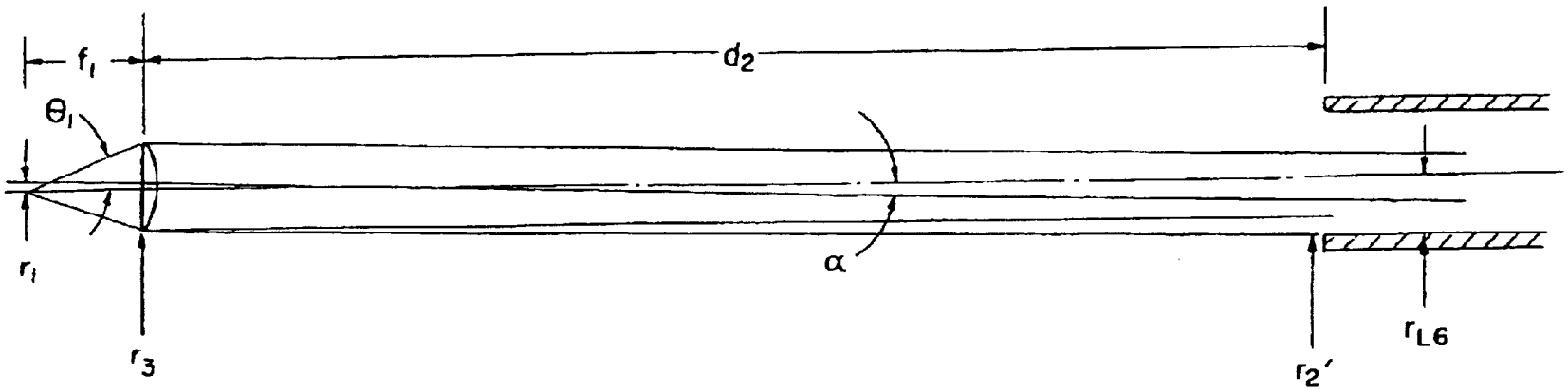
FIG. 3 is a diagram illustrating the laser excitation path in the case where the distance from the end of the laser excitation fiber to the rear of the collimating lens is set equal to the back focal length of the lens.

FIG. 3 illustrates the laser excitation path in the case where the distance from the end of the laser excitation fiber to the rear of the collimating lens is set equal to the back focal length of the lens. For simplicity, I have shown this path in a straight line, without the rhomboid element. The radius of the laser beam when it reaches the entrance to the lightguide will be equal to $$r_2=r_3+d_2 \tan \alpha, \text{ where } \tan \alpha=r_1/f_1, \text{ and } r_3=f_1 \tan \theta_1. \quad \text{Eq. 1}$$

Here, $r_1$ is radius of the fiber core, $\sin \theta_1$ is the numeric aperture of the fiber, $f_1$ is the focal length of the collimating lens, $r_3$ is the radius of the beam as it leaves the lens, and $d_2$ is distance from the lens to the lightguide entrance.

The above equation can be written $$r_2=f_1 \tan \theta_1+d_2 r_1/f_1. \quad \text{Eq. 2}$$

It can be seen from Eq. 2 that either a large or a small value of $f_1$ will produce a large value of $r_2$. Since we wish to minimize $r_2$, consistent with a reasonably small value of $r_3$, we wish to find the value of $f_1$ that minimizes $r_2$. This can be done by taking the derivative of $r_2$ as a function of $f_1$ and setting this equal to zero. The yields:

$$f_1=(d_2 r_1/\tan \theta_1)^{1/2}. \quad \text{Eq. 3}$$

Substituting Equation 3 into Equation 2 yields the minimum value of $r_2$, $$r_2=2(d_2 r_1 \tan \theta_1)^{1/2}. \quad \text{Eq. 4}$$

As a practical example, we will take $r_1$=0.05 mm, $d_2$=100 mm, and $\sin \theta_1$=0.22 (or $\tan \theta_1$=0.226). Substituting these values into Equations 3 and 4 yields $f_1$=4.7 mm and $r_2$=2.1 mm. It can also be seen that the radius of the beam at the collimating lens is r3=1.06 mm.

For the nominally collimated case just discussed, the angular divergence of the beam is equal to $\alpha$, where $$\tan \alpha=r_1/f_1. \quad \text{Eq. 5}$$

This value can be reduced by increasing the focal length of the collimating lens. This may be desirable in cases where the internal diameter of the lightguide is larger than the initially calculated beam diameter at its entrance. However, if the internal diameter of the lightguide is smaller than the initially calculated beam diameter, it may be necessary to change the design to one in which the end of the fiber-optic core is imaged on the entrance to the lightguide. This will increase the beam divergence in the lightguide in the interest of enabling all of the radiation to enter it. This compromise is discussed below.

Figure 4A:
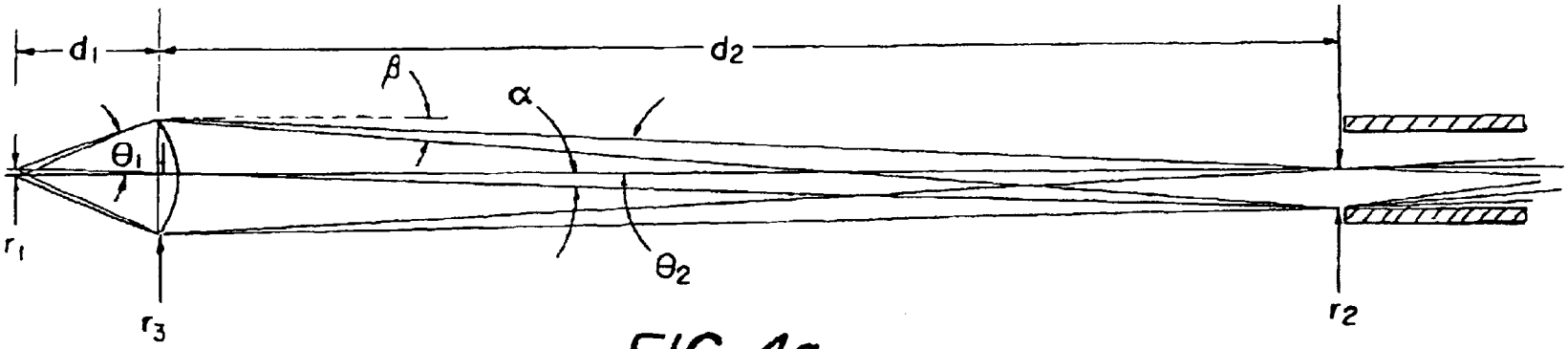
FIG. 4a illustrates the condition in which the end of the optical fiber core is imaged on the input end of the lightguide.

FIG. 4 illustrates the condition in which the end of the optical fiber core is imaged on the input end of the lightguide. Here, the relationship between d1 and d2 is given by $$1/d_1+1/d_2=1/f_1, \quad \text{Eq. 6}$$

and the image radius is given by $$r_2=r_1 d_2/d_1. \quad \text{Eq. 7}$$

Here we see that the first term of Equation 2 has vanished. For a given value of $d_2$, we must select $d_1$ (and hence $f_1$) to satisfy Equation 7. The radius of the beam at the lens will then be equal to $$r_3=d_1 \tan \theta_1. \quad \text{Eq. 8}$$

The maximum divergence of rays entering the lightguide will now be given by $$\tan \beta=(r_3+r_2)/d_2=r_3/d_2+r_1/f_1. \quad \text{Eq. 9}$$

Comparing Equation 7 to Equation 3 and Equation 9 to Equation 5, we see that by imaging the optical fiber core on the input to the lightguide, we have decreased the beam diameter at the expense of increased beam divergence. Under some conditions, it may be possible to achieve a better compromise between beam diameter and divergence angle by forming the imagine within the lightguide rather than at the entrance.

We now consider the conditions at the output of the lightguide. (See FIG. 4b.) The maximum divergence of the laser beam will still be given by $\beta$ even if the individual rays have been reflected by the walls of the lightguide. In the preferred embodiment of the invention, an objective lens will be located adjacent to the output of the lightguide. If the focal length of this lens (in the surrounding medium) is given by $d_3$, the focused laser spot will have a radius of $$r_4=d_3 \tan \beta. \quad \text{Eq. 10}$$

Figure 4B:
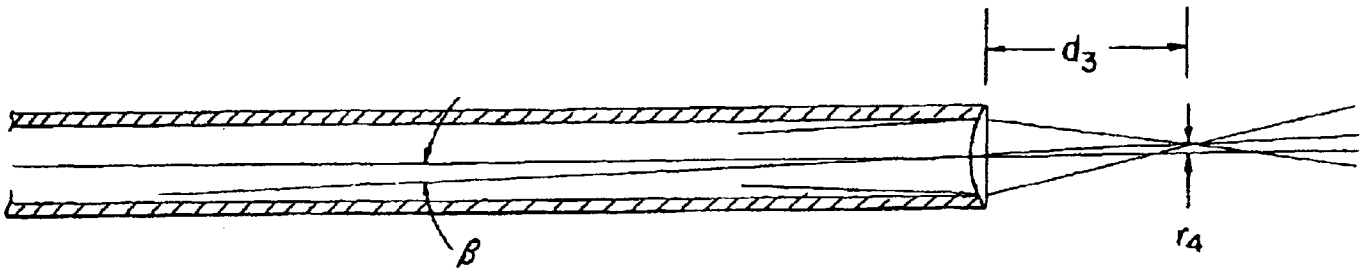
FIG. 4b illustrates the condition at the output of the lightguide.
Figure 5:
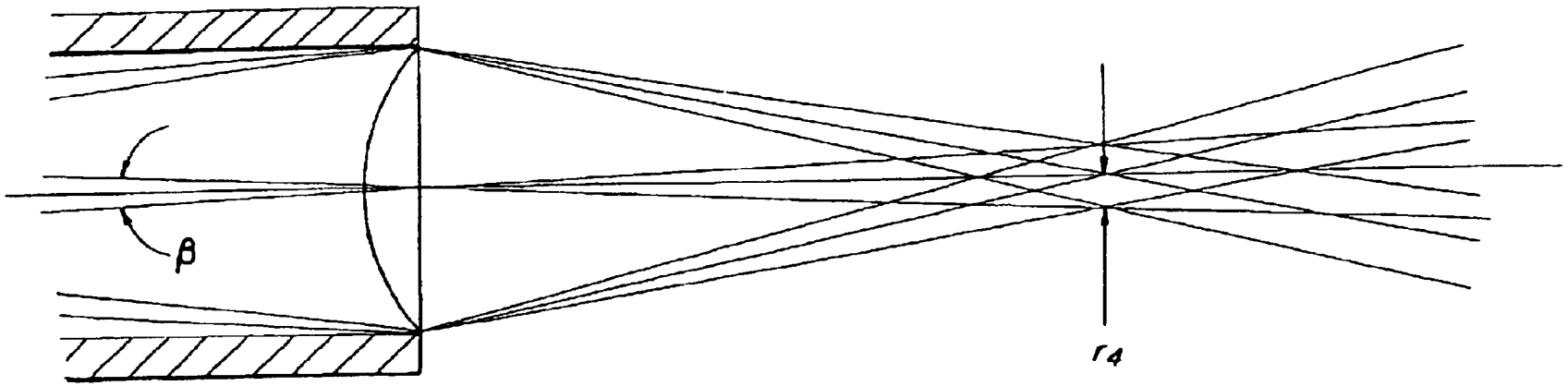
FIG. 5 is an enlargement of the objective region of FIG. 4b, showing the central in extreme rays that determine the size the focus spot.

FIG. 5 is an enlargement of the objective region of FIG. 4b showing the central and extreme rays that determine the size of the focused spot.

Figure 6:
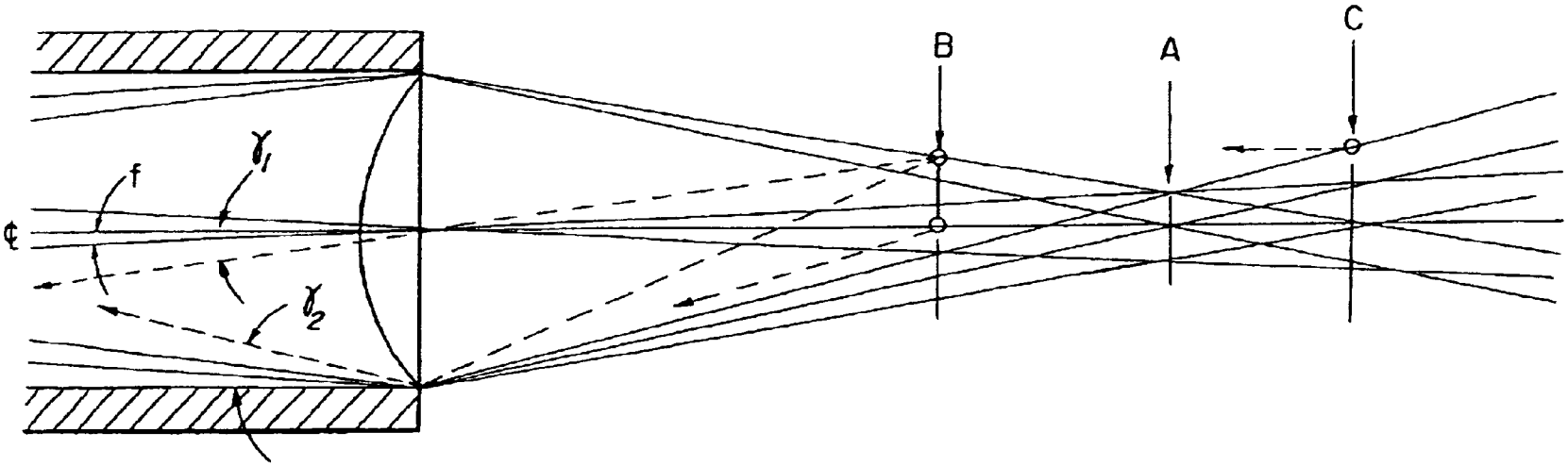
FIG. 6 is an illustration of the objective region wherein three planes within the illuminated region are indicated by the letters A, B, and C.

FIG. 6 is a further illustration of the objective region in which I have shown three planes in the illuminated region, indicated by the letters A, B, and C. Plane A is the focal plane, i.e. the plane where the illuminating beam has the least diameter. Raman shifted radiation which originates in this plane and is collected by the objective lens will have a maximum divergence angle of $\beta$ in within the lightguide. After emerging from the far end of the lightguide, this radiation would be confined to the same volume as the laser illumination and thus would strike the injection element. In the case where this element is a rhomboid—or other fully reflecting element—all of the radiation would be blocked from reaching the lens that focuses on the collection optical fiber. However Raman shifted radiation is produced throughout the volume that is illuminated by laser radiation. For example, in plane $\beta$, a substantial part of the radiation arising from the two regions indicated by the circles will strike the objective lens at incidence angle larger than those corresponding to any of the laser rays passing through the same regions. As a result, such radiation will travel through the lightguide at angles such as $\gamma_1$ and $\gamma_2$ that are greater than the maximum divergence of the incident laser radiation. On emerging from the far end of the lightguide, most of this radiation will miss the injection element. This is also true of a proportion of the radiation originating in regions past the focal plane, as indicated by the dashed ray from the circled region of plane C. However, the collection solid angle will be greater for regions between the focal plane and the objective lens. I would thus expect these regions to contribute predominately to the collected Raman signal.

It should be noted that, for embodiments of the invention which use a dichroic beam splitter rather than a fully reflecting injection element, all illuminated regions—including the focal plane—will contribute to the detected Raman shifted signal.

Figure 7:
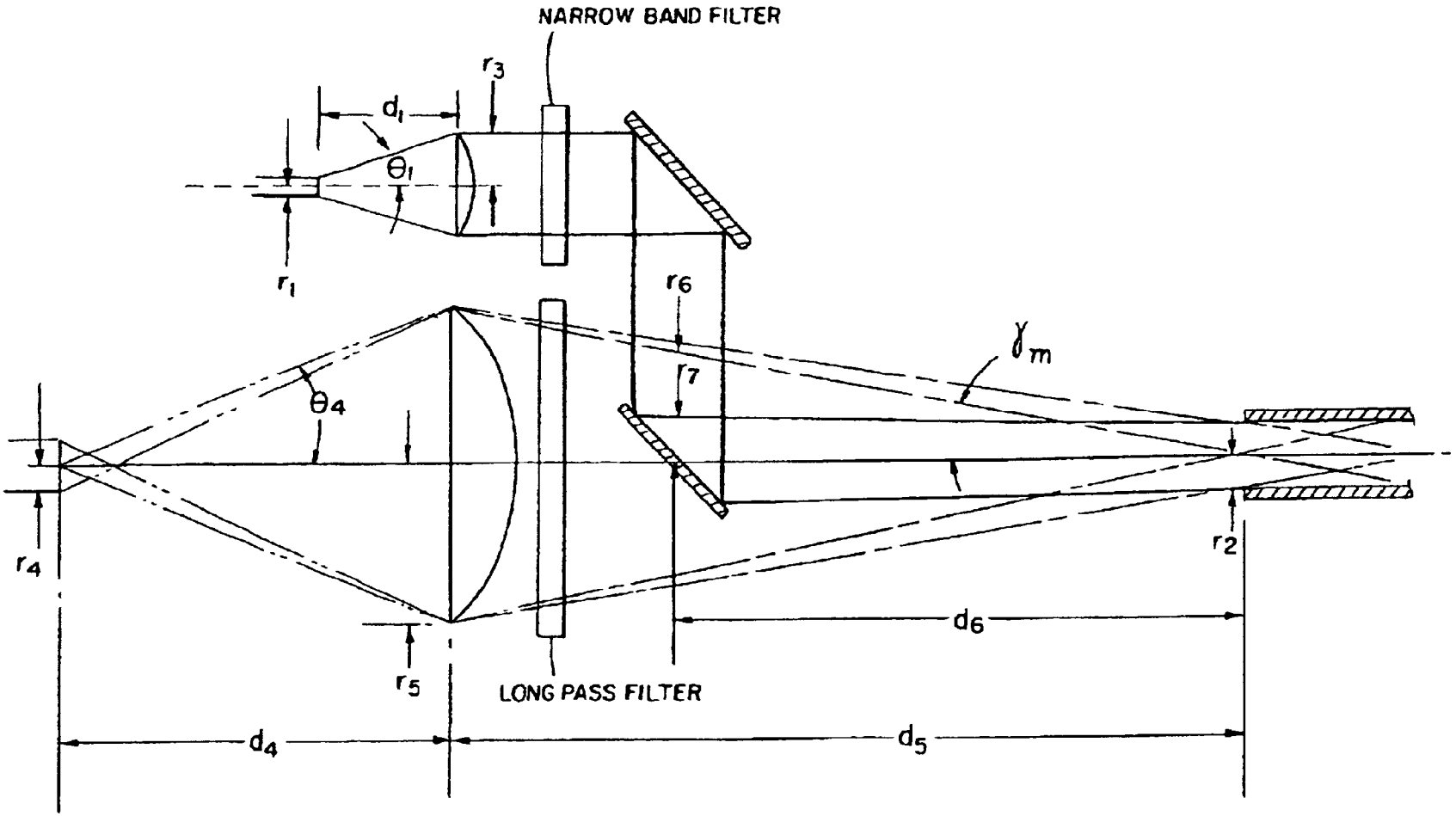
FIG. 7 illustrates a preferred embodiment for an "optical head" used in a preferred embodiment of the invention.

FIG. 7 illustrates a preferred embodiment of the "optical head" of the probe, i.e. that portion of the probe which contains the fiber-optic terminations and both the collimating and the collecting optics. Also included in the region, but not shown in FIG. 7, are the optical filters that are generally imposed in both optical paths. As the figure illustrates, reflecting devices—which may include one or more mirrors, a dichroic beamsplitter, or a fully reflecting rhomboid—are used to superimpose the axis of the laser beam on the axis of the receiving optical path. As discussed above, the laser path will be nearly collimated and as small in diameter as is consistent with the other requirements of the design.

In order to collect as much of the Raman shifted radiation as is practical, it is important to maximize the field of view of the optical element which collects the radiation emerging from the lightguide. In other words, we wish to maximize the collection angle, $\gamma_m$, as illustrated in FIG. 7. This angle is determined by the numeric aperture of the optical fiber (NA= $\sin\theta_4$), and by the two distances, $d_4$ and $d_5$. i.e., $$\tan\gamma_m=(d_4/d_5)\tan\theta_4. \qquad \text{Eq. 11}$$

Since we have imaged the end of the lightguide on the collection fiber, we have $d_4/d_5=r_4/r_2$, and we can write the above equation as $$\tan\gamma_m=(r_4/r_2)\tan\theta_4. \qquad \text{Eq. 12}$$

From Equation 12, we see that, for a given fiber numeric aperture and lightguide diameter, the collected signal can be maximized by maximizing the core radius of the receiving optical fiber. In the case where the laser injection element is a rhomboid or other fully reflecting device, it is also important that $\gamma_m$ be great enough so that a large proportion of the collection field of view misses this element. The size of the injection element should be at least as large as the laser beam striking it. In the imaging case, the radius of this beam is determined by the beam radius at the collimating lens, by the radius of the lightguide, and by the position of the element along the optical path. As a reasonable approximation, we can assume that the beam radius at the injection element is equal to the radius at the lens. i.e. $r_3=d_1\tan\theta_1$.

In FIG. 7, I have indicated the radius of the collection field of view to be $r_6$ in the plane containing the injection element. The maximum value of $r_6$ will occur when the injection element is quite close to the collection lens, in which case we can use the approximation $r_6=r_5$. It can be shown that the maximum value of the ratio of $r_6$ to $r_3$ will be $$(r_6/r_3)_{max}=r_4d_5/r_1d_2. \qquad \text{Eq. 13}$$

For the assumed conditions, $d_2$ will always be larger than $d_5$. However, this equation again indicates the benefit of maximizing the radius of the core of the collection fiber relative to that of the excitation fiber.

Figure 8:
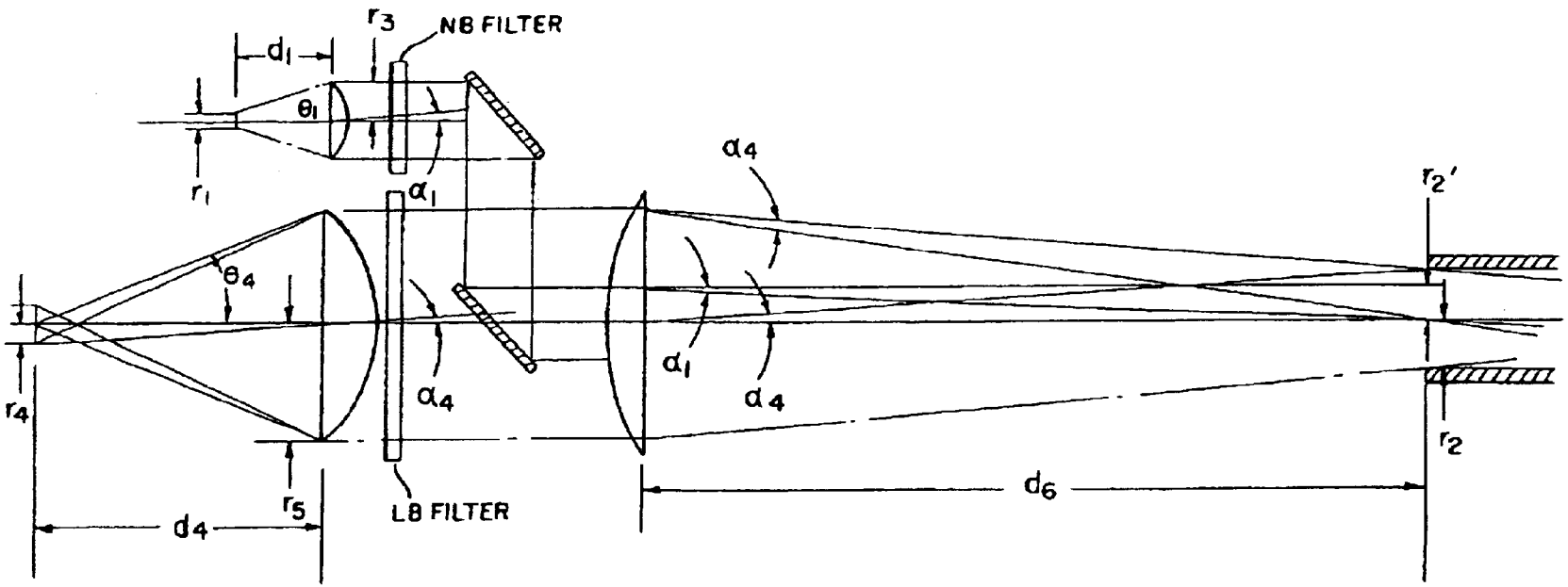
FIG. 8 illustrates an alternative embodiment of the invention in which the distances $d_1$ and $d_4$ are set equal to the focal lens of the two lenses so that both the laser beam to the right of the collimating lens and the receive field of view to the right of the collection lens are nominally collimated.

FIG. 8 illustrates an alternative embodiment in which the distances $d_1$ and $d_4$ are set equal to the focal lengths of the two lenses so that both the laser beam to the right of the collimating lens and the received field of view to the right of the collection lens are nominally collimated. A separate lens is then used for coupling to the end of the light guide. Ideally, the distance $d_0$ would be set so that the image of the collection lightguide core is matched to the lightguide. The radius of the laser beam at the entrance to the lightguide, $r_2$, could then be either matched to the lightguide inner diameter or smaller than this, depending on the following relationships:

$$r_2/d_0=r_1/d_1 \text{ and } r_2/d_0=r_4/d_4. \qquad \text{Eq. 14}$$

The advantage of this design is that it allows the obstruction due to the injection element to minimized even if this element is some distance from the collection lens. However, it does have a disadvantage in that the additional lens used to the match the lightguide is a source of potentially undesirable reflection of the incident laser beam.

I claim:

1. An immersion probe for use in Raman spectroscopy [which includes] *comprising*:

an extended immersion tip that includes an internally reflecting lightguide;

first optical element for collecting laser radiation emerging from a first optical fiber and directing it, after subsequent reflections, into the end of said internally reflecting lightguide in such a way that it is as nearly collimated as possible consistent with substantially all of the radiation entering the lightguide;

second optical element for collecting Raman shifted radiation emerging from said internally reflecting light guide and focusing it on a second optical fiber in such a way that the size and shape of the image of the end of the lightguide matches the size and shape of said second optical fiber; *and* reflecting means for redirecting the beam formed by said first optical element so that its axis is anti-parallel to and coaxial with the axis of the Raman shifted radiation emerging from said lightguide.

2. The immersion probe of claim 1 wherein the numeric apertures corresponding to the diameter and longitudinal positions of said first and second optical elements are at least as great as the numeric apertures of the associated optical fibers.

3. The immersion probe of claim 2 wherein the diameter of said second optical fiber is substantially greater than the diameter of said first optical fiber.

4. The immersion probe of claim 3 wherein the distance from said first optical element to said first optical fiber is set so that the image of said first optical fiber is falls at the end or within said lightguide and is no greater in diameter than said lightguide.

5. The immersion probe of claim 4 wherein the ratio of the distance from said first optical element to said first optical fiber to the distance from said first optical element to said lightguide is approximately equal to the diameter of said first optical fiber to the internal diameter of said lightguide, and Wherein the ratio of the distance from said second optical element to said second optical fiber to the distance from said second optical element to said lightguide is approximately equal to the diameter of said second optical fiber to the internal diameter of said lightguide.

6. The immersion probe of claim 2 in which said reflecting means comprises two totally reflecting, parallel surfaces.

7. The immersion probe of claim 6 in which the area of the reflecting surface which overlaps the collected radiation is small compared to the cross section of said collected radiation in the vicinity of said reflecting surface.

8. The immersion probe of claim 7 in which said reflecting means is an internally reflecting rhomboid.

9. The immersion probe of claim 1 wherein the diameter of said second optical fiber is substantially greater than the diameter of said first optical fiber.

10. The immersion probe of claim 9 wherein the distance from said first optical element to said first optical fiber is set so that the image of said first optical fiber is falls at the end or within said lightguide and is no greater in diameter than said lightguide.

11. The immersion probe of claim 10 wherein the ratio of the distance from said first optical element to said first optical fiber to the distance from said first optical element to said lightguide is approximately equal to the diameter of said first optical fiber to the internal diameter of said lightguide, and Wherein the ratio of the distance from said second optical element to said second optical fiber to the distance from said second optical element to said lightguide is approximately equal to the diameter of said second optical fiber to the internal diameter of said lightguide.

12. The immersion probe of claim 1 in which said reflecting means comprises two totally reflecting, parallel surfaces.

13. The immersion probe of claim 12 in which the area of the reflecting surface which overlaps the collected radiation is small compared to the cross section of said collected radiation in the vicinity of said reflecting surface.

14. The immersion probe of claim 13 in which said reflecting means is an internally reflecting rhomboid.

15. An immersion probe for use in Raman spectroscopy [which includes] *comprising*:

an extended immersion tip that includes an internally reflecting lightguide;

first optical element for collecting laser radiation emerging from a first optical fiber and directing it[, after subsequent reflections,] into the end of said internally reflecting lightguide in such a way that it is as nearly collimated as possible consistent with substantially all of the radiation entering the lightguide;

second optical element for collecting Raman shifted radiation emerging from said internally reflecting light guide and focusing it on a second optical fiber in such a way that the size and shape of the image of the end of the lightguide matches the size and shape of said second optical fiber; *and* reflecting means for redirecting the [beam formed by] *Raman shifted radiation to* said second optical element so that its axis is anti-parallel to and coaxial with the axis of the [Raman shifted] *laser* radiation [emerging from said lightguide.]*;*

*wherein the ratio of the distance from said first optical element to said first optical fiber to the distance from said first optical element to said lightguide is approximately equal to the diameter of said first optical fiber to the internal diameter of said lightguide, and*

*wherein the ratio of the distance from said second optical element to said second optical fiber to the distance from said second optical element to said lightguide is approximately equal to the diameter of said second optical fiber to the internal diameter of said lightguide.*

16. The immersion probe of claim 15 wherein the numeric apertures corresponding to the diameter and longitudinal positions of said first and second optical elements are at least as great as the numeric apertures of the associated optical fibers.

17. The immersion probe of claim 16 wherein the diameter of said second optical fiber is substantially greater than the diameter of said first optical fiber.

18. The immersion probe of claim 17 wherein the distance from said first optical element to said first optical fiber is set so that the image of said first optical fiber is falls at the end or within said lightguide and is no greater in diameter than said lightguide.

[19. The immersion probe of claim 18 wherein the ratio of the distance from said first optical element to said first optical fiber to the distance from said first optical element to said lightguide is approximately equal to the diameter of said first optical fiber to the internal diameter of said lightguide, and Wherein the ratio of the distance from said second optical element to said second optical fiber to the distance from said second optical element to said lightguide is approximately equal to the diameter of said second optical fiber to the internal diameter of said lightguide.]

20. The immersion probe of claim 16 in which said reflecting means comprises two totally reflecting, parallel surfaces.

[21. The immersion probe of claim 20 is which the area of the reflecting surface which overlaps the collected radiation is small compared to the cross section of said collected radiation in the vicinity of said reflecting surface.]

[22. The immersion probe of claim 21 in which said reflecting means is an internally reflecting rhomboid.]

23. The immersion probe of claim 15 wherein the diameter of said second optical fiber is substantially greater than the diameter of said first optical fiber.

24. The immersion probe of claim 23 wherein the distance from said first optical element to said first optical fiber is set so that the image of said first optical fiber is falls at the end or within said lightguide and is no greater in diameter than said lightguide.

[25. The immersion probe of claim 24 wherein the ratio of the distance from said first optical element to said first optical fiber to the distance from said first optical element to said lightguide is approximately equal to the diameter of said first optical fiber to the internal diameter of said lightguide, and Wherein the ratio of the distance from said second optical element to said second optical fiber to the distance from said second optical element to said lightguide is approximately equal to the diameter of said second optical fiber to the internal diameter of said lightguide.]

26. The immersion probe of claim 15 in which said reflecting means comprises two totally reflecting, parallel surfaces.

[27. The immersion probe of claim 26 in which the area of the reflecting surface which overlaps the collected radiation is small compared to the cross section of said collected radiation in the vicinity of said reflecting surface.]

[28. The immersion probe of claim 27 in which said reflecting means is an internally reflecting rhomboid.]

* * * * *